US009697716B2

(12) United States Patent
Duric et al.

(10) Patent No.: US 9,697,716 B2
(45) Date of Patent: Jul. 4, 2017

(54) DETERMINATION OF AN ALARM-ISSUING TIME OF AN ALARM DEVICE

(75) Inventors: Aleksandar Duric, Zug (CH); Martin Forster, Jona (CH)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 401 days.

(21) Appl. No.: 12/997,690

(22) PCT Filed: Jun. 13, 2008

(86) PCT No.: PCT/EP2008/057494
§ 371 (c)(1),
(2), (4) Date: Mar. 10, 2011

(87) PCT Pub. No.: WO2009/149767
PCT Pub. Date: Dec. 17, 2009

(65) Prior Publication Data
US 2011/0156897 A1      Jun. 30, 2011

(51) Int. Cl.
*G08B 21/14*         (2006.01)
*G08B 31/00*         (2006.01)
(Continued)

(52) U.S. Cl.
CPC ............ *G08B 21/14* (2013.01); *G08B 29/26* (2013.01); *G08B 31/00* (2013.01); *A61B 5/746* (2013.01)

(58) Field of Classification Search
USPC ..... 340/286.01, 286.04, 286.05; 116/2, 4, 5; 368/10, 12
See application file for complete search history.

(56) References Cited

U.S. PATENT DOCUMENTS 4,088,986 A *  5/1978  Boucher ................... 340/521
5,165,883 A    11/1992  Van Bemmel
(Continued)

FOREIGN PATENT DOCUMENTS

CN       2469447 Y      1/2002
EP       0 880 764 B1   12/1998
(Continued)

OTHER PUBLICATIONS

Grosshandler, William. "Towards the Development of a Universal Fire Emulator-Detector Evaluator." Fire Safety Journal 29 (1997): 113-127. Print.*

(Continued)

*Primary Examiner* — Mohamed Barakat
(74) *Attorney, Agent, or Firm* — Laurence Greenberg; Werner Stemer; Ralph Locher

(57) ABSTRACT

A method for determining a triggering time for the issuance of an alarm by an alarm device. A measured value is sensed at a measuring time, and the measured value is indicative of a hazard potential within a monitoring range. A waiting time is identified by way of a function which respectively indicates an assigned waiting time for a plurality of different measured values and which has a continuous profile. The triggering time is determined on the basis of the measuring time and the identified waiting time. In addition, an alarm device having a detection device for sensing a measured value and having an evaluation device which is configured to carry out said method is described. In addition, a program element for determining a triggering time for the issuance of an alarm by an alarm device is described, wherein the program element can be loaded into an evaluation unit of the alarm device and can cause the abovementioned method to be carried out.

15 Claims, 4 Drawing Sheets

(51) Int. Cl.
*G08B 29/26* (2006.01)
*A61B 5/00* (2006.01)

(56) References Cited

U.S. PATENT DOCUMENTS

| | | | | |
|---|---|---|---|---|
| 5,276,434 | A * | 1/1994 | Brooks et al. | 340/632 |
| 5,691,703 | A * | 11/1997 | Roby et al. | 340/628 |
| 5,786,768 | A * | 7/1998 | Chan et al. | 340/632 |
| 6,437,698 | B1 * | 8/2002 | Byrne | G08B 3/10 340/588 |
| 6,998,991 | B1 * | 2/2006 | Goldstein et al. | 340/628 |
| 7,142,105 | B2 * | 11/2006 | Chen | 340/521 |
| 7,170,418 | B2 * | 1/2007 | Rose-Pehrsson | G08B 17/00 340/539.26 |
| 7,327,247 | B2 * | 2/2008 | Tice | G08B 29/20 340/309.16 |
| 7,642,924 | B2 * | 1/2010 | Andres | G08B 17/00 340/506 |

FOREIGN PATENT DOCUMENTS

| | | |
|---|---|---|
| RU | 2067728 C1 | 10/1996 |
| SU | 310276 | 7/1971 |
| WO | 2005/119618 A2 | 12/2005 |

OTHER PUBLICATIONS

Gottuk, Daniel T., Michelle J. Peatross, Richard J. Roby, and Craig L. Beyler. "Advanced fire detection using multi-signature alarm algorithms." Fire Safety Journal 37 (2002): 381-394. Print.*
Cleary, Thomas and William Grosshandler. "Survey of Fire Detection Technologies and System Evaluation/Certification Methodologies and Their Suitability for Aircraft Cargo Compartments." NISTIR 6356, National Institute of Standards and Technology, Gaithersburg, MD, 1999.*
Grosshandler, W. L., An assessment of technologies for advanced fire detection. In Heat and Mass Transfer in Fire and Combustion Systems, vol. 223. ASME, New York, 1992, pp. 1-10.*
Written Opinion of the International Searching Authority for PCT/EP2008/057494.

* cited by examiner

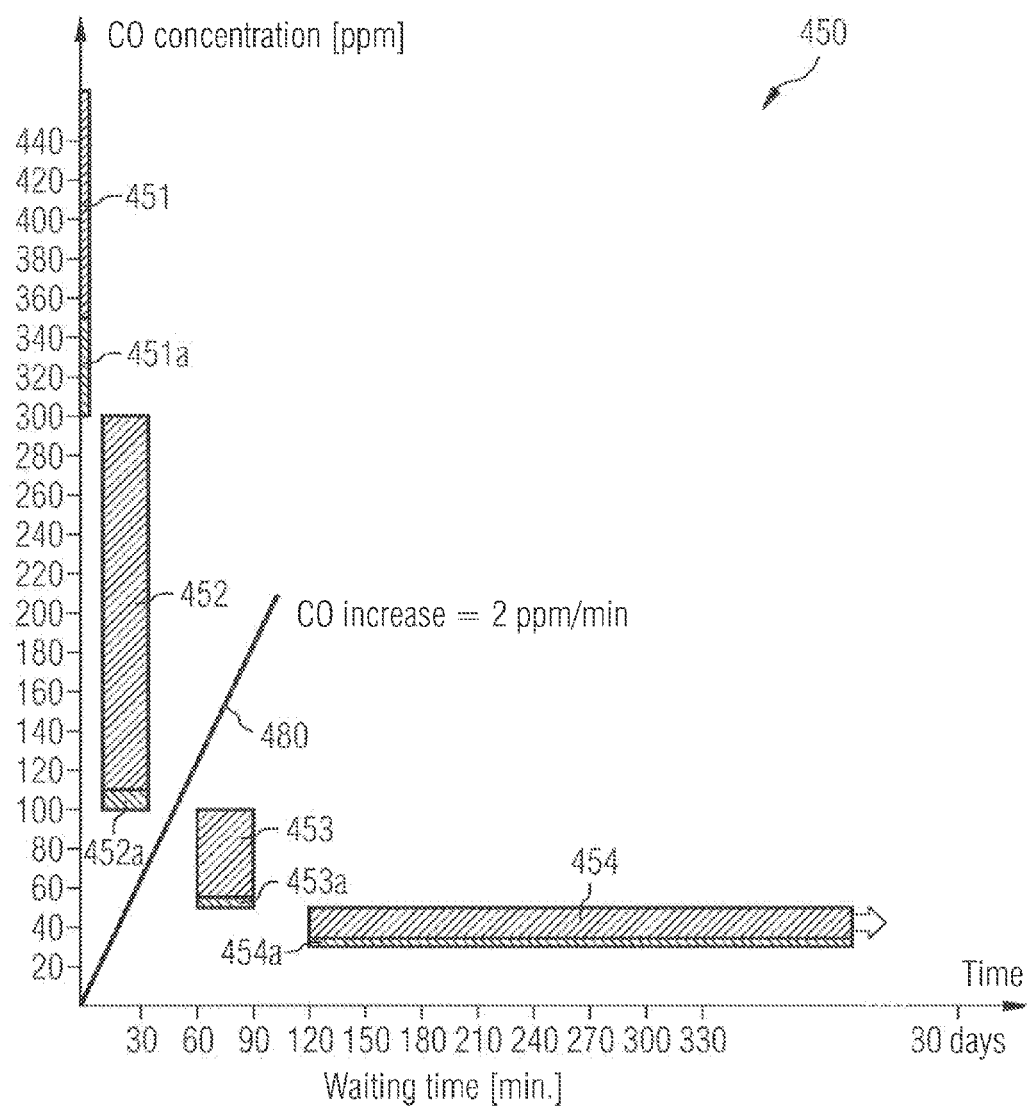

DETERMINATION OF AN ALARM-ISSUING TIME OF AN ALARM DEVICE

BACKGROUND OF THE INVENTION

Field of the Invention

The present invention relates to the technical field of alarm signaling technology. The present invention relates especially to a method for determining a triggering time of an alarm device, the triggering time of which depends on a detected measured value which is indicative of a hazard potential within a monitoring range. The present invention further relates to an alarm device with a detection device for detecting such a measured value and with an evaluation device which is configured for carrying out said method. The present invention further relates to a program element for determining a triggering time for the issuance of an alarm by the alarm device, which can be loaded into an evaluation unit of the alarm device and can cause the aforementioned method to be carried out.

In order to detect an undesired occurrence of a hazard situation, such as an escape and/or the presence of a hazardous gas for example, alarm devices are frequently used which are fitted at suitable points within a hazard-monitored area, within a building for example. Depending on the hazard situation to be monitored, an alarm device is equipped with a suitable detector which, on the basis of a physical measurement, can detect the hazard situation as early as possible. In the case of a danger situation caused by gas the detector is typically a gas sensor which is sensitive to a gas to be detected or to a number of gases to be detected.

An alarm device can also be a part of an alarm system or of a comprehensive building management system which, as a well as a central control console, has a number of alarm devices embodied as peripheral units. The peripheral units can be connected directly or indirectly to the central console via a wired or a wireless communication link.

An alarm system with a main control unit and a plurality of gas sensors is known from U.S. Pat. No. 4,088,986. If respective different gas sensors signal a hazardous gas concentration exceeding the predetermined threshold values to the main control unit, an alarm is output.

An algorithm for outputting a fire alarm is known from WO 2005/119618 A2, which uses as its input variables the output signals of a smoke detector, a CO gas sensor and a CO2 gas sensor. If the gradients of the different sensors, individually or in combination, exceed specific thresholds, an alarm is initiated.

A multi-signature fire alarm is known from EP 0 880 764 B1 in which a signal indicative of a smoke concentration and a signal indicative of a possibly hazardous gas concentration are multiplied together. If a specific value is exceeded during this multiplication, an alarm is output. An alarm is also output if just a change in the gas concentration over time exceeds a specific value.

Gas alarms or gas-smoke alarms are however subject to legal requirements. These requirements, which are normally set down in a standard, must be fulfilled by a corresponding alarm before it is approved in the respective country.

In Europe for example there are predetermined test methods for the detection of carbon monoxide in domestic premises and requirements for the operational behavior of CO gas alarms. These are described in the standard with the number EN 50291.

FIG. 4 shows in a diagram 450 a number of approval conditions of Standard EN 50291 for a CO gas alarm. Standard EN 50291 defines a number of alarm issuing conditions, a first alarm issuing condition 451a, a second alarm issuing condition 452a, a third alarm issuing condition 453a and a fourth alarm issuing condition 454a. These alarm issuing conditions specify a respective minimum waiting time for a measured value for the CO concentration for which it is necessary to wait after the occurrence of the measured value before an alarm may be issued. These alarm issuing conditions likewise also specify a maximum waiting time within which an alarm must be issued after an occurrence of a corresponding measured value. The waiting times are plotted in diagram 450 on the abscissa. The measured values for the CO concentration are plotted on the ordinate.

The first alarm issuing condition 451a prescribes that an alarm must be signaled after 3 minutes at the latest on occurrence of a CO concentration of 330±30 ppm. The second alarm condition 452a prescribes that an alarm may be issued (a) after 10 minutes at the earliest if a CO concentration of 110±10 ppm is present and (b) an alarm must be issued at the latest by 40 minutes after the occurrence of a corresponding CO concentration. The third alarm condition 453a prescribes that an alarm may be issued (a) after 60 minutes at the earliest if a CO concentration of 55±5 ppm is present and (b) an alarm must be issued at the latest by 90 minutes after the occurrence of a corresponding CO concentration. The fourth alarm condition 454a prescribes that an alarm must be issued (a) after a waiting time of 120 minutes at the earliest if a CO concentration of 33±3 ppm is present. In practice, for each of the alarm issuing conditions 454a, 453a and 452a, the corresponding range of measured values will be extended down to the lower measured value of the next highest alarm issuing condition 453a, 452a and 451a in relation to the measured value. In such cases the possible alarm issuing ranges 451, 452, 453 and 454 shown in the diagram 450 are produced.

It is pointed out that there are also other standards for other countries which prescribe other waiting times prior to an alarm being issued for the different CO concentrations. Standard UL 2034, which is valid for the USA, should be mentioned in particular in this context.

In order to create a gas alarm device which fulfills the valid standard in each case, an appropriate algorithm must be implemented in an evaluation unit of the gas alarm device, which prescribes for any given measured value a waiting time compatible with the standard for issuing the alarm.

For gas concentrations largely constant over time different country-specific standards can thus still be met comparatively easily by corresponding algorithms adapted for the specific country. However, as soon as increasing or decreasing gas concentrations occur, situations arise which can be problematic in respect of uniquely assigning a waiting time to a specific measured value. This problem is illustrated below with reference to a typical increase in the CO concentration of 2 ppm per minute over a period of time. This increase is shown in diagram 450 by means of a straight-line gradient 480.

At time t=15 minutes the CO concentration has reached a value of 30 ppm. An alarm would then have to be issued at time t_alarm=15+120=135 minutes. At time t=24 minutes the CO concentration has reached a value of 48 ppm and the alarm would still only have to be issued at time t_alarm=15+120=135 minutes. One minute later, at time t=25 minutes, the CO concentration has reached a value of 50 ppm and from now on the alarm would suddenly have to be issued at the time t_alarm=25+60=85 minutes. As can be seen from FIG. 4, there are similar jumps for the required alarm-issuing time on transition from t=49 minutes (alarm must be issued after 85 minutes) to t=50 minutes (alarm must be issued after 50+10=60 minutes).

BRIEF SUMMARY OF THE INVENTION

The underlying object of the invention is to improve the calculation of alarm times of an alarm device, to the extent to which jumps in the determination of the alarm-issuing time can be avoided for variable measured values and such that the alarm is issued as early as possible, but still within the period demanded by the standard.

This object is achieved by the subject matter of the independent claims. Advantageous embodiments of the present invention are described in the dependent claims.

In accordance with a first aspect of the invention, a method for determining a triggering time for the issuance of an alarm by an alarm device is described. The method features (a) detection of a measured value at a measuring time, with the measured value being indicative of a potential hazard within a monitoring range, (b) establishing a waiting time by means of a function which in each case specifies an assigned waiting time for a plurality of different measured values and which has a continuous profile and (c) determining a triggering time based on the measuring time and the waiting time established.

A continuous function within the framework of this application is to be understood as also including functions with a continuous profile and of which a first derivation either likewise includes a continuous profile or a non-continuous profile. This means that functions with inflexion points, which cause a first derivation which suddenly changes, likewise represent continuous functions within the meaning of this application.

The method described is based on the knowledge that a suitable waiting time can be determined for any given detected measured value by means of a continuous function to establish said time, with the dependence of the waiting time on the measured value not exhibiting any jumps or discontinuities. This can mean that, for a fictional slight increase in the measured value, the corresponding waiting time also only changes slightly.

The elimination of discontinuities in the measured-value-dependent establishment of a suitable waiting time has the advantage that, especially with measured values that change over time, no ambiguous results are produced in the establishment of the waiting time and/or the determination of the triggering time. This enables an especially reliable determination of the triggering times of alarms to be guaranteed.

The described continuous function can be visualized in a two-dimensional coordinate system, in which the different measured values are plotted on one axis and the assigned waiting times on the other axis. The continuous function in this case can be selected such that a plurality of standards which must be met for approval of a corresponding alarm device is also actually met. The term standard in this context is to be understood as a legal specification which typically differs for different countries and which defines criteria as to whether and when, for a specific measured value from an alarm device which operates in accordance with the prescribed method, an alarm must be issued.

By using the described continuous function for establishing a waiting time, a simple and especially a generally-valid method can be provided for different types of alarm device, with which a reliable determination of the triggering time for an alarm can be guaranteed both for measured values changing little over time and also for those changing greatly over time. In addition all possible standards for the alarm device can be fulfilled by a suitable choice of the continuous function and through an appropriate implementation of the described method in an alarm device.

The continuous function can be implemented by a mathematical adaptation for example, in which one or more parameters of the function are adapted in a suitable manner, so that in all cases the sensitivities of the corresponding alarm device demanded by the relevant standards will be fulfilled.

In accordance with an exemplary embodiment of the invention the function is constituted such that, within a waiting time range predetermined by a standard, it exceeds an associated lower limit value for the measured value also predetermined by the standard.

In this sense an alarm issuing time range can be predetermined by the standard for example in which the two-dimensional coordinate system described above takes the form of a rectangle. Provided the measured values are plotted on the ordinate and the corresponding waiting times are plotted on the abscissa in this coordinate system, the lower limit value for the measured value will be determined by the lower horizontal delimitation line of the alarm issuing time range. The horizontal delimitation line is then intersected by the function within the predetermined waiting time range.

The described lower limit value for the measured value, which must be assumed at least once by the continuous value within the predetermined waiting time range, thus represents a condition to be fulfilled for determining the continuous function. This condition can for example be fulfilled by a suitable adaptation of one or more parameters which characterize the continuous function.

In accordance with a further exemplary embodiment of the invention, the function is constituted such that it does not exceed a waiting time-independent minimum threshold value for the measured value.

A waiting time-independent minimum threshold value represents an absolute lower boundary for the measured value below which the alarm may not be issued. Such a minimum threshold value can also be prescribed by legal standards in order to avoid undesired false alarms independently of a timing curve of the measured value which is however always smaller than the minimum threshold value. This takes account of the generally-known fact that the relative statistical uncertainties and/or uncertainties caused by a detection device during the detection of a measured value are at their greatest if the detected measured values are very small.

In the coordinate system described above, in which the waiting time is plotted on the abscissa and the measured values are plotted on the ordinate, the waiting time-independent minimum threshold value for the measured value represents a horizontal lower delimitation line. This may only asymptotically approach the continuous function and may not intersect with it.

At this point it is pointed out that the continuous function can naturally also be visualized in the coordinate system in which the waiting time is plotted on the ordinate and the measured values are plotted on the abscissa. However the changed visualization does not mean that the technical circumstances and the advantages described above change in any way.

In accordance with a further exemplary embodiment of the invention the function is constituted such that, within a range of measured values predetermined by a further standard, it exceeds an associated early limit value for the waiting time likewise predetermined by the further standard. In this case too an alarm issuing time range can be predetermined by the further standard which, in the two-dimensional coordinate system described above, takes the form of a rectangle for example. Provided the measured value is also plotted on the ordinate in this case and the waiting time is plotted on the abscissa, the early limit value for the waiting time is determined by the left-hand, for example vertical, delimitation line of the corresponding alarm issuing time range. This for example vertical delimitation line is then intersected by the continuous function.

In accordance with a further exemplary embodiment of the invention the function is constituted such that, within a range of measured values with especially high measured values, it asymptotically approaches the waiting time zero. In this way it can be ensured that, as from a specific level of the detected measured value, independent of the previous timing curve of the measured value, which in this case typically exhibits a very fast increase, an alarm will always be triggered. This behavior too can be demanded by legal standards in order to guarantee, in the event of an abrupt increase in the measured value, that the alarm is triggered without delay.

In the coordinate system described above in which the measured values are plotted on the ordinate and the associated waiting times on the abscissa, a corresponding standard which demands that for high measured values an alarm must be issued immediately, represents an alarm issuing time range of which the vertical left-hand delimitation line may not be intersected by the threshold function but only touched by it.

In accordance with a further exemplary embodiment of the invention the function will be defined by one or more parameters and by a function variable. The type of function can be freely selected in this case so that the function approximates to or approaches the alarm issuing time ranges predetermined by each relevant standard with respectively adapted parameters as defined above. The parameters can also be referred to as coefficients. This can mean that optimum parameters or coefficients will be determined for any given standard, within the framework of an allocation procedure for example.

There is no basic upper limit as regards of the number of parameters required for the description of the function. The higher the number of parameters used, the more precisely the function can be adapted to different legal standards and/or desired alarm issuing time ranges. Naturally, as the number of parameters used increases, the complexity, especially of a suitable adaptation procedure for defining the parameters for an actual implementation, also increases. In practice it has proved to be a good compromise between the complexity and the accuracy of the continuous function able to be achieved for three, four or five parameters to be used to describe the function.

Naturally the preferred number of parameters to be used also depends on the type of function. The function can have one or more components. These components can for example be a polynomial, a hyperbola, a trigonometric function, a logarithmic function, an exponential function, etc. Naturally the function can also feature a combination of various of the said mathematical components or further mathematical components not mentioned in this application.

In accordance with a further exemplary embodiment of the invention the parameter or parameters is or are selected such that the function produces a constant measured value independent of the waiting time, which represents a limit measured value. This limit measured value can especially be described by a parameter which represents a constant within the function. This means that an alarm is issued immediately when this limit measured value is reached. This can be seen from the fact that, in the two-dimensional coordinate system described above, one of the values assigned to a measured value which is identical to the limit measured value is zero.

In accordance with a further exemplary embodiment of the invention, the function variable is the waiting time or the measured value. This means that the continuous function can be plotted in the two-dimensional coordinate system described above, in which case it is of no significance whether the waiting time is plotted on the abscissa or the ordinate and the measured value on the ordinate or the abscissa.

If the waiting time is plotted on the abscissa and the measured value on the ordinate, then the waiting time assigned to a detected measured value can be determined in a simple manner by the above-mentioned continuous function being inverted and the detected measured value being used in the inverted function. The triggering time can then be produced by a simple addition of the corresponding measuring time and the corresponding waiting time determined. The triggering time can be represented mathematically by the following equation:

$$t\_alarm = t\_mess + f^{-1}(a,b,c,\ldots,\text{measured value})$$

In this equation
t_alarm stands for the triggering time;
t_mess stands for the measuring time;
$f^{-1}$ stands for the inverted continuous function f;
a, b, c, ... stand for individual parameters of the function f or $f^{-1}$ respectively; and
measured value stands for the measured value detected at the time t_mess.

If the measured value is plotted on the abscissa and the waiting time is plotted on the ordinate, then a waiting time assigned to a detected measured value can be determined in a simple manner by the detected measured value being used in a continuous function g. The triggering time can then be produced in a corresponding manner by a simple addition of the corresponding measuring time and the corresponding waiting time determined. The inverse function thus does not have to be used here. This can be represented mathematically by the following equation:

$$t\_alarm = t\_mess + g(a,b,c,\ldots,\text{measured value})$$

In this equation
t alarm stands for the triggering time;
t mess stands for the measuring time;
g stands for the inverted continuous function f;
a, b, c, ... stand for individual parameters of the function g; and measured value stands for the measured value detected at time t_mess.

In accordance with a further exemplary embodiment of the invention the function features a number of subsections, with two adjacent subsections being linked to each other at an inflection point of the function.

The linear subfunctions in this case can be defined by specific points of standardized alarm issuing conditions, with each point being defined by a measurement value and an assigned waiting time. The use of a function with a number of subsections, which can also be referred to as a segmented function, has the advantage that any given standardized alarm issuing conditions can be approximated especially well. In this case the number of segments required for a good approximation can depend on the number and the distribution of the individual alarm issuing conditions within a two-dimensional coordinate system, in which the different measured values are plotted on one axis and the respective assigned waiting times are plotted on the other axis.

In accordance with a further exemplary embodiment of the invention the method further features (a) a detection of a further measured value at a further measuring time, with the further measured value also being indicative of a potential hazard within the monitoring range, (b) an establishing of a further waiting time by means of the function, and (c) a determination of a further triggering time based on the further measuring time and the further waiting time established.

The execution of the entire method can be repeated at regular intervals. Depending on the strength of the changes of the measured values to be expected, the measured value detection and if necessary also the subsequent measured value evaluation for the purposes of determining the further triggering time or further triggering times can be undertaken at different intervals. For example a time difference of two seconds has been shown to be suitable. However the execution of the method can also be repeated at any other given time intervals.

The further measured value detection and a subsequent further measured value evaluation for the purposes of determining a further waiting time or a further triggering time do not necessarily have to mean that the previous determination of the waiting time or of the triggering time is no longer relevant. Instead the previous method can continue to be executed together with the further method. This means that two triggering times will be determined. The actual alarm triggering can then be determined in particular at the earliest triggering time.

For measured values which vary over time a new triggering time can also be continuously determined. If a triggering time is less than or equal to the time value of the current time then an alarm is triggered.

In accordance with a further exemplary embodiment of the invention the further measured value differs from the measured value by at least one predetermined value. This can mean that the further method is only executed if (a) the measured value is not constant over time and if (b) a specific period of time has elapsed between the measuring time and the further measuring time so that there is a desired minimum difference set between the measured value and the further measured value.

The predetermined value describing a measured value difference can be an absolute value or a relative value in this case. For an absolute measured value difference the further measured value differs from the measured value by at least one fixed value which is independent of the level of the measured value. For a relative measured value difference the further measured value differs from the measured value by a value dependent on the level of the measured value and/or of the further measured value.

In accordance with a further embodiment of the invention (a) as well as the further triggering time the triggering time continues to be considered if the further measured value is greater than the measured value, and (b) the triggering time is discarded if the further measured value is less than the measured value.

This can mean that in the case of a measured value increase, a plurality of triggering times is taken into consideration, with the actual alarm triggering then especially occurring at the earliest triggering time. This enables it to be ensured that under no circumstances is there a delayed alarm triggering.

If however a measured value increase is followed by a measured value decrease and the measured value then remains at a level, especially without any health implications for people, by discarding at least the original triggering time an unnecessary alarm can be avoided. This applies in any event if waiting times beyond a comparatively very long period of time are not to be taken into consideration and thus do not lead to any alarm being triggered and/or if the harmless measured values are assigned an infinite waiting time.

In accordance with a further exemplary embodiment of the invention the measured value is indicative of the concentration of a gas. The gas can be any given gaseous substance which could potentially represent a hazard for persons and/or machines. In particular the gas can involve carbon monoxide, which is not perceptible to human beings but despite this can be very hazardous for human beings above a certain concentration.

To detect the gas concentration any gas sensor suitable for the gas concerned can be used. This typically includes electrochemical gas sensors, biochemical gas sensors, infrared gas sensors, mass-sensitive gas sensors and/or thermochemical gas sensors. The gas sensor can also be constructed as a semiconductor element.

The gas can also be a substance the absence of which could lead to a hazard for people and/or machines. In this case a waiting time assigned to the measured value becomes ever shorter as the measured value decreases.

At this point it should be pointed out that the measured value and if necessary the further measured value can also be indicative of any other given hazard potential. Thus the measured value can for example describe the concentration of smoke within the hazard range monitored by the alarm device. In addition the measured value can be a measured temperature value. This especially makes sense if a temperature change can be caused for example by a chemical reaction with which substances poisonous to human beings are released.

The measured value can further be indicative of the air humidity, for example within a store for fruit and vegetables and/or flowers. In addition the measured value can be a detected pressure which is present in liquids or gases of a hydraulic system. A wind strength, for example in connection with wind turbines, the speed of rotation of a given rotor or an expansion in a building or a bridge can also be a respective measured value which is indicative of a specific hazard potential.

Regardless of the type of measured value, it is true to say that the greater the hazard potential of a measured variable is, the shorter should be the period of time during which the hazard potential may occur without an alarm. This means that the greater the respective hazard potential is, the smaller must be the period of time prior to an alarm being issued.

It should also be noted that an alarm triggering can also be correlated with other measured values. Thus it is entirely conceivable for example for the described method to be employed in what is known as a multi-criteria alarm, for example in conjunction with a detected gas concentration, with the triggering time determined by the described method still able to be modified by a different physical measured value for example a smoke concentration, a temperature, a liquid level, etc.

In accordance with a further aspect of the invention an alarm device for triggering the issuance of an alarm is described. The alarm device features (a) a detection device configured for detecting a measured value which is indicative of a hazard potential within a monitoring range, and (b)

an evaluation device which is coupled to the detection device and which is configured to enable the method in accordance with one of the previous claims to be executed.

The alarm device described is based on the knowledge that the method explained above, which is used for determining a suitable triggering time for the issuance of an alarm, uses a continuous function which can be used in a simple manner in existing alarm devices. This merely requires suitable software to be loaded into the evaluation device, which is typically a standard processor for data processing.

The alarm device described can also feature a further detection device which is used for detecting another measured value based on another physical measurement. As already explained above in connection with a method-related exemplary embodiment, the further detection device can be used for example to measure a smoke concentration, a temperature or any other given measurement variable, which is likewise indicative of a hazard potential.

The described alarm device can further feature a transceiver unit which is suitable for wired and/or wireless communication with a central control console of an alarm system.

The evaluation device can also be assigned a non-volatile memory of the alarm device. In the event of the continuous function being determined by one of by a number of parameters, these parameters can be stored in the non-volatile memory. If the alarm device is to subsequently meet further standards, then it is only necessary to store a further set of parameter values in the non-volatile memory.

In accordance with a further aspect of the invention a program element for determining a triggering time for the issuance of an alarm of an alarm device is described. The program element, when executed by an evaluation unit, is suitable for executing the method described above.

The program element can be implemented as computer-readable instruction code in any suitable programming language, such as in JAVA, C/C++ etc. for example. The program element can be stored on a computer-readable storage medium (CD-Rom, DVD, external disk, volatile or non-volatile memory, built-in memory processor, etc.). The instruction code can program a computer or other programmable devices such that the desired functions will be executed. In addition the program element can be provided in a network, such as the Internet for example, from which it can be downloaded by a user if required.

Within the meaning of the present application reference to such a program element is synonymous with reference to a computer program product and/or a computer-readable medium containing instructions for controlling a computer system in order to coordinate the operation of an alarm device in a suitable manner, so that the effects associated with the inventive method can be achieved.

It is pointed out that the invention can be realized both by means of a computer program, i.e. by software, and also by means of one or more specific electrical circuits, i.e. in hardware, or in any given hybrid form, i.e. by means of software components and hardware components. An implementation of the invention by means of software is preferred on account of its simplicity.

It is further pointed out that forms of embodiment of the invention have been described with reference to different inventive objects. In particular the number of forms of embodiment of the invention are described with method claims and other forms of embodiment of the invention with device claims. It will however be immediately clear to the person skilled in the art, when reading this application, that, unless explicitly stated to the contrary, in addition to a combination of features which belong to a type of inventive object, any given combination of features is also possible which belong to the different types of inventive objects.

Further advantages and features of the present invention emerge from the following typical description of currently preferred forms of embodiment. The individual figures of the drawing of this application are to be seen merely as schematic and not as true-to-scale.

BRIEF DESCRIPTION OF THE SEVERAL VIEWS OF THE DRAWING

FIG. 4 shows a diagram in which alarm issuing conditions for a CO gas alarm defined by Standard EN 50291 are presented.

DESCRIPTION OF THE INVENTION

Figure 1:
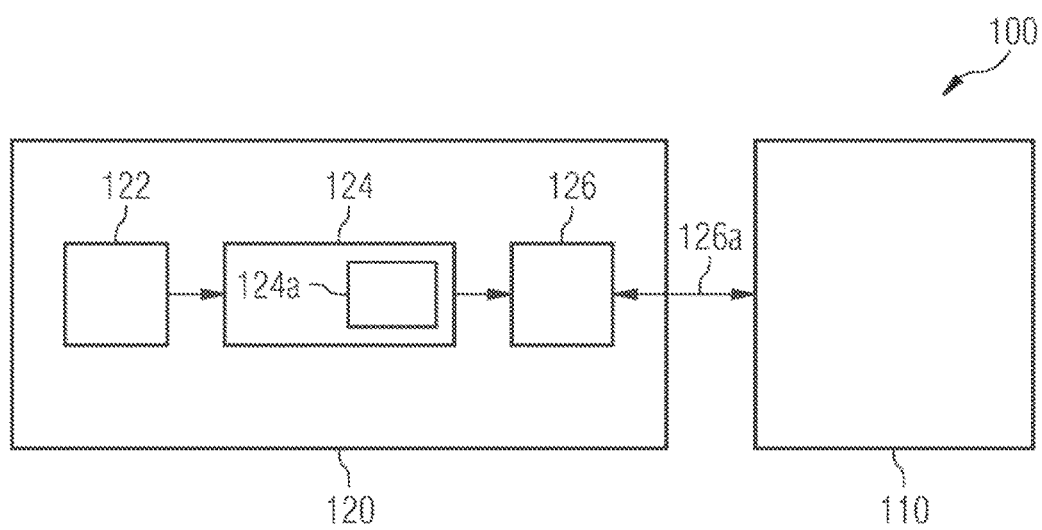
FIG. 1 shows an alarm system having a central unit and an alarm device with an evaluation device which is configured for executing the method for determining a triggering time for the issuance of an alarm by an alarm device.

At this point it is pointed out that the reference signs of components shown in different figures of the drawing which are the same or which correspond to one another only differ in their first digit.

It is also pointed out that the forms of embodiment described below merely represent a limited selection of possible embodiment variants of the invention. It is especially possible for features of individual forms of embodiment to be combined with one another in a suitable manner so that, for the person skilled in the art, with the embodiment variants explicitly presented here, a plurality of different forms of embodiment are to be seen as obviously disclosed.

FIG. 1 shows an alarm system 100 featuring a central alarm system console 110 and an alarm device 120. In accordance with the exemplary embodiment shown here the alarm device is a gas alarm 120 which is sensitive to CO concentrations. However this in no way excludes the alarm device 120 being able to be sensitive to other gases and/or being able to be used for detecting other hazard potentials, such as smoke for example.

To detect the gas concentration the alarm device 120 features a detection device 122. The detection device 122 features a gas sensor not shown in any greater detail suitable for the measurement of CO concentrations.

Downstream from the detection device 122 is connected an evaluation device 124. The evaluation device 124 features a processing unit 124a which is configured for executing the method described in this application for determining a triggering time for the issuance of an alarm by the alarm device 120. The alarm device 120 also features a transceiver unit 126 which forwards the result provided by the evaluation device 124 via a radio communication link or a wired link 126a to the central alarm control console 110.

The processor unit 124a determines, using a continuous function $f(A, B, C, D, E; t)$, if and when an alarm must be issued. In this case A, B, C, D and E are parameters through which the continuous function is defined such that the standard applicable in the respective country is fulfilled with regard to triggering times or waiting times respectively.

A number of examples for the continuous function are given below. Naturally the parameters A, B, C, D and E, where they are used at all for the function concerned, must be adapted within the framework of a suitable adaptation procedure to the applicable standard in each case.

f1 (A, B, C, D; t)=[(A+t)/(B/t+C·t)]+D
f2 (A, B, C; t)=A·arctan(B·t)+C
f3 (A, B, C, D; t)=A/[1+B·exp(C·t)]+D
f4 (A, B, C; t)=1/(A·t+B)+C
f5 (A, B, C, D; t)=A/[(1+B·t^C) ^2]+D
f6 (A, B, C, D, E; t)=(A+B·t)/(1+C·t+D·t^2)+E
f7 (A, B, C, D; t)=A·exp{[(ln(t)−B)^2]/C}+D
f8 (A, B, C, D; t)=A·t^[B+C·ln(t)]+D
f9 (A, B, C, D, E; t)=A·exp(B·t)+C·exp(D·t)+E In this list "/" stands for the division operator, "^" for a power, "exp" for the exponential function with the base e and "ln" for the logarithm to the base e.

In a simulation carried out by the inventor it has emerged that all currently known standards for the operation of a CO gas alarm can be approximated to a good extent by one and the same continuous function. This applies to all the functions f1 through f9 listed above. The coefficients A, B, C and where necessary D and E are different in this case for respective different standards, but the structure of the respective functions f1 through f9 can remain unchanged for a good approximation of the alarm issuing ranges predetermined by different standards. Thus the respective algorithm for determining the waiting time or the alarm triggering time for all standards which the gas alarm or the gas-smoke alarm must fulfill can remain identical and only the continuous function f1, f2, . . . , or f9 used must be evaluated in order to determine the time for issuance of an alarm as a function of the CO concentration.

It is expressly pointed out here that the functions f1 through f9 specified here do not represent a definitive list of possible functions which are suitable for the method described in this application for determining a triggering time for the issuance of an alarm.

Figure 2:
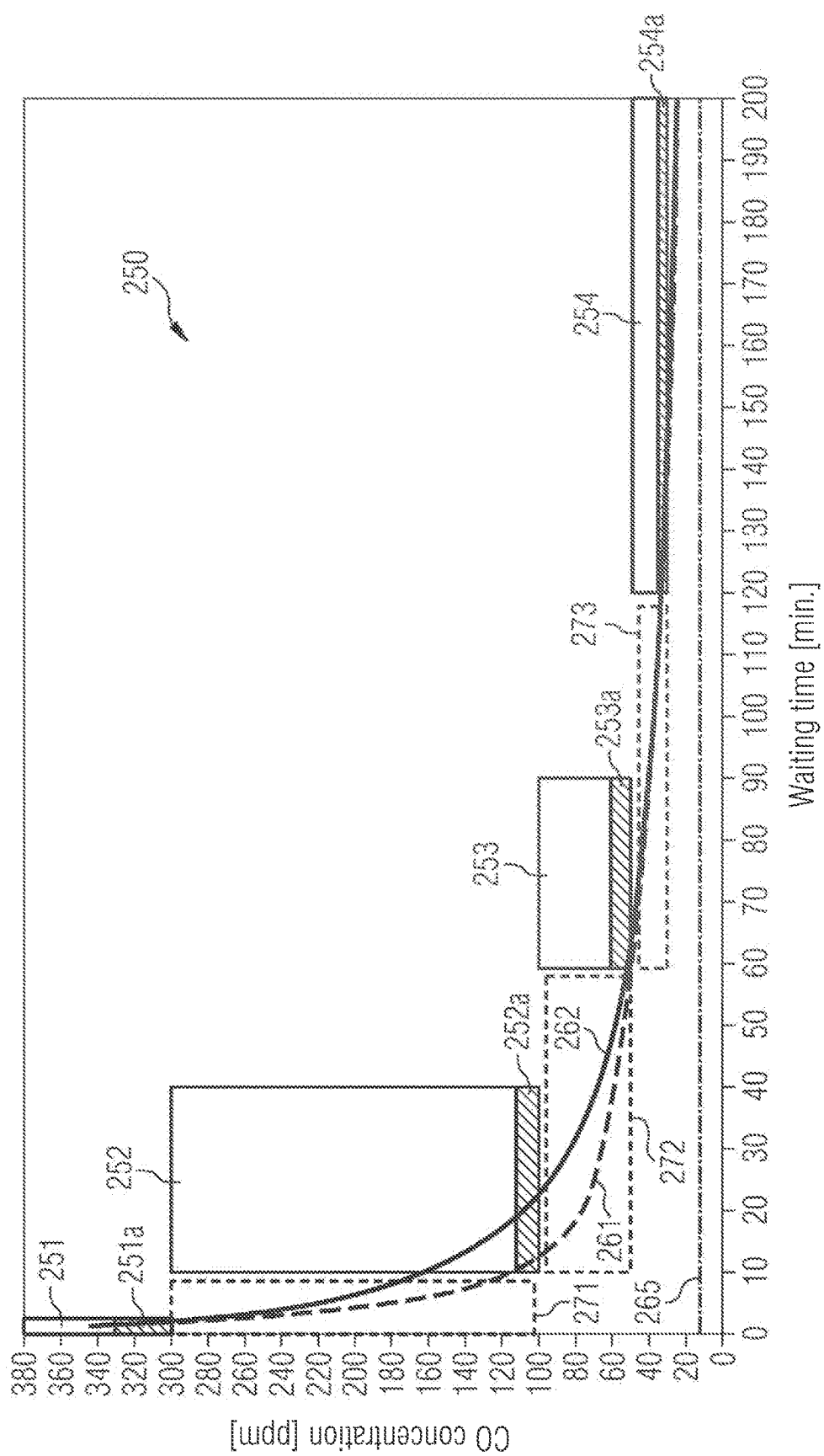
FIG. 2 shows a diagram in which two continuous functions are presented together with alarm issuing conditions required for a CO gas alarm.

FIG. 2 shows a diagram 250 in which the two continuous functions f4 and f9 listed above are plotted in a coordinate system in which the measured value or the CO concentration is plotted on the ordinate in the unit ppm and the waiting time is plotted on the abscissa, which together with the respective measurement time determines the triggering time for the issuance of an alarm. The function f9 is shown by a dashed line and is identified by the reference sign 261. The function f4 is shown by a solid line and is identified by the reference sign 262.

As can be seen from FIG. 2, the parameters A, B and C of function f4 and the parameters A, B, C, D and E of function f9 are selected so that the conditions for issuing alarms specified in Standard EN 50291, the first alarm issuing condition 251a, the second alarm issuing condition 252a, the third alarm issuing condition 253a and the fourth alarm issuing condition 254a and the alarm issuing ranges shown by way of example, the first alarm issuing range 251, the second alarm issuing range 252 the third alarm issuing range 253 and the fourth alarm issuing range 254 are approximated very well.

The parameters of the functions f4 and f9 are selected in this case such that, for all alarm issuing conditions 251a, 252a, 253a and 254a, the lowest horizontal delimiting line is intersected in each case. The points at which the respective function f4 or f9 intersect with these delimiting lines define the respective maximum waiting times which are produced when the respective threshold value is exceeded.

In addition the use of the continuous function f4 or f9 means that a first extended alarm issuing range 271, a second extended alarm issuing range 272 and a third extended alarm issuing range 273 are covered. These extended alarm issuing ranges result in an alarm being issued more quickly than if the alarm issuing conditions predetermined by the standard were to be used for issuing the alarm. Through the use of a continuous function f4 or f9 a waiting time is assigned in a unique manner to each measured value whereby, in the event of a measured value which increases over time, discontinuities in the determination of the actual alarm triggering time which are produced by adding the respective waiting time to the respective measuring time are avoided.

A minimum limit value 265 for the measured value or for the CO concentration is also specified in diagram 250. This minimum limit value 265 is independent of the waiting time. The waiting time-independent minimum limit value 265 thus represents an absolute lower boundary for the CO concentration below which no alarm may be triggered. The minimum limit value 265 can likewise be prescribed by legal standards in order to avoid undesired false alarms independently of a time sequence of a CO concentration which is however always smaller than the minimum limit value 265.

Figure 3:
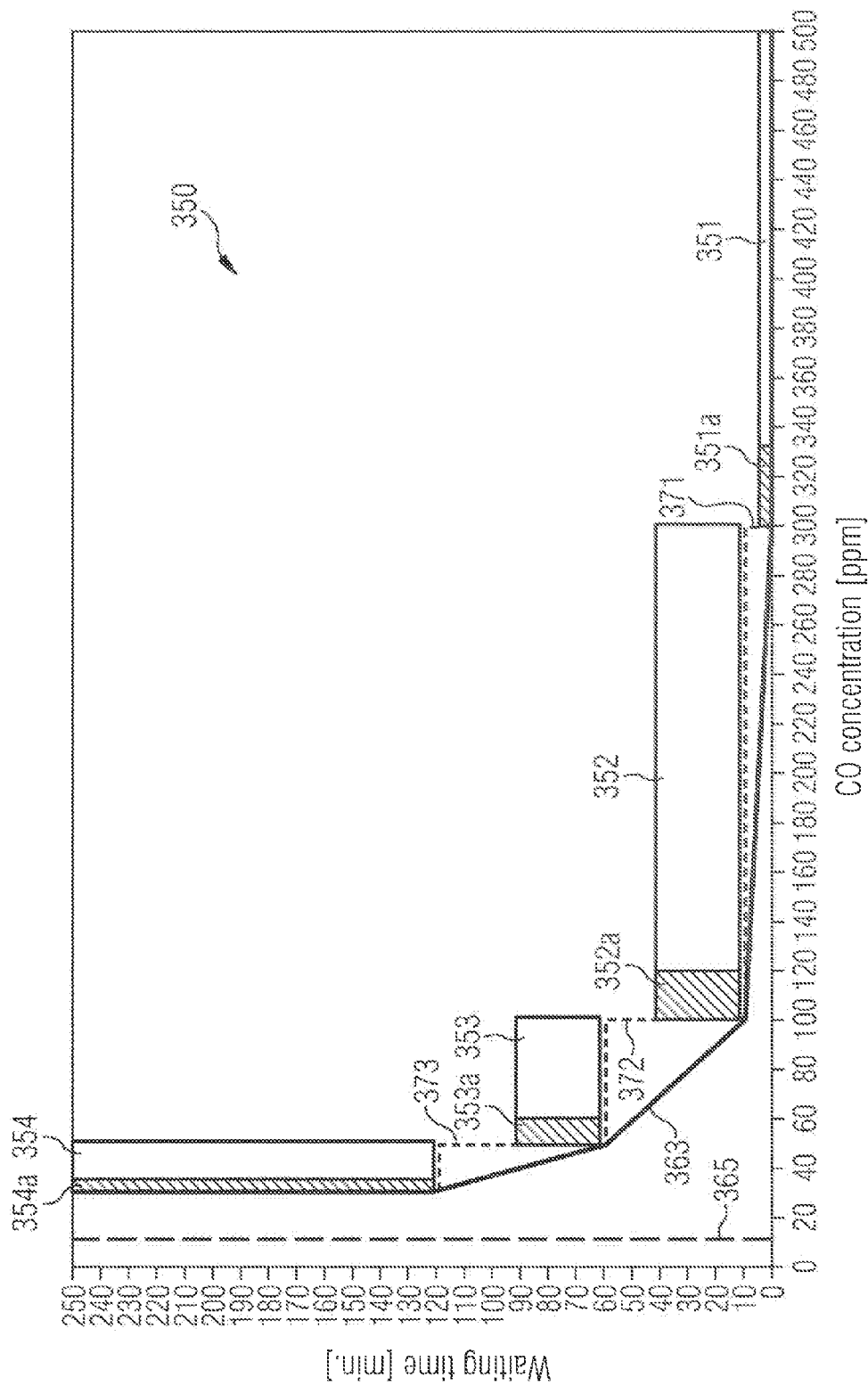
FIG. 3 shows a diagram in which a segmented continuous function is presented, which has four inflection points and which approximates the alarm issuing conditions required for a CO gas alarm.

FIG. 3 shows a diagram 350 in which a segmented continuous function g is shown which is labeled with the reference sign 363. The function 363 is plotted in a coordinate system in which the measured value or the CO concentration in the unit ppm respectively is plotted on the abscissa and the waiting time is plotted on the ordinate. The waiting time determines together with the respective measurement time the precise triggering time for the issuance of an alarm.

The function 363 approximates the alarm issuing conditions for a CO gas detector required by a standard. The continuous function 363 is composed of a total of three linear subfunctions gi (ai, bi; measured value), i=1 to 3, and thus has inflection points. The linear subfunctions gi are defined in this case by the respective lower left corners of the standardized alarm issuing conditions, a first alarm issuing condition 351a, a second alarm issuing condition 352a, a third alarm issuing condition 353a and a fourth alarm issuing condition 354a. The alarm issuing conditions 351a, 352a, 353a and 353a are the same as those shown in FIG. 2 and labeled by the reference signs 251a, 252a, 253a and 254a. The same applies to the respective assigned alarm issuing ranges 351, 351, 351 and 351 for the respective alarm issuing conditions 351a, 352a, 353a and 354a, which are not prescribed by the Standard EN 50291.

In accordance with the exemplary embodiment shown here the function g(a, b; measured value) assumes the following values for different measured values or different CO concentrations respectively:

g(measured value<30 ppm CO): The measured value lies below the threshold predetermined by the fourth alarm issuing condition 354a. The function g is thus not defined for these measured values. As an alternative these types of small measured values can also be assigned a waiting time of "infinite".

g(measured value>300 ppm CO)=0: With such a high concentration an alarm is issued immediately.

g(concentration CO_i<=measured value<=concentration CO_i+1)=ai·measured value+bi for i=1 . . . 3: As can be seen from FIG. 3, in accordance with the exemplary embodiment shown here, a value of 30 ppm is produced for CO_1, a value of 50 ppm for CO_2, a value of 100 ppm for CO_3 and a value of 300 ppm for CO_4. The parameters ai and bi are each produced from a simple adaptation of the respective line sections of the function g at the lower left corner points of two adjacent alarm issuing conditions.

Naturally an inflected continuous function g can also be composed of a number of subfunctions gi. In such cases it is also possible for at least a few of the subfunctions to have a somewhat more complex mathematical form compared to a simple straight line.

As can be seen from FIG. 3, further supplementary alarm issuing ranges 371, 372 and 373 are defined by the subfunctions gi which each have the shape of a triangle. The supplementary alarm issuing ranges 371, 372 and 373 also produce a faster alarm issuing than if only the alarm issuing conditions 351a, 352a, 353a and 354a predetermined by the standard were to be used for issuing the alarm.

A minimum threshold value 365 for the CO concentration is also specified in the diagram 350 below which an alarm may not be issued. The minimum threshold value 365 which can likewise be prescribed by legal standards does not however play any role in the exemplary embodiment described here, since the function g is merely defined in a measured value range greater than or equal to 30 ppm and is thus far above the minimum threshold value shown. As already described above, this means that no alarm is issued for measured values of less than 30 ppm CO.

The invention claimed is:

1. A method for determining a triggering time for issuing an alarm of an alarm device, the method which comprises:
    detecting a measured value at a measuring time, the measured value being indicative of a hazard potential within a monitoring range;
    establishing a waiting time by way of a function based on a given standard, the function:
        specifying an assigned waiting time in each case for a plurality of different measured values, the waiting time reducing as the measured value rises and increasing as the measured value falls, for a slight increase in the measured value, the corresponding waiting time also only changes slightly; and
        having a continuous profile, the continuous profile not exhibiting jumps or discontinuities;
    determining the triggering time based on the measuring time and the waiting time thus established; and
    the waiting time being the time necessary to wait after the occurrence of the measured value before an alarm may be issued; and
    covering extended alarm issuing ranges, the extended alarm issuing ranges resulting in the alarm being issued more quickly than if the alarm issuing conditions predetermined by the standard are used for issuing the alarm.

2. The method according to claim 1, which comprises defining the function such that, for a waiting time range predetermined by a given standard, the waiting time exceeds an associated lower threshold for the measured value predetermined by the given standard.

3. The method according to claim 1, which comprises defining the function such that, for a measurement value range predetermined by a given further standard, the waiting time exceeds an associated early threshold for the waiting time likewise predetermined by the further standard.

4. The method according to claim 1, which comprises defining the function such that, for a measured value range with especially high measured values the waiting time asymptotically approaches the waiting time of zero.

5. The method according to claim 1, wherein the function comprises one or more parameters and a function variable.

6. The method according to claim 5, which comprises selecting the one or more parameters such that the function produces a constant measurement value independent of the waiting time which represents a measured value threshold.

7. The method according to claim 5, which comprises selecting the function variable from the group consisting of:
    the waiting time; and
    the measured value.

8. The method according to claim 1, wherein the function featuring a number of subsections, with two adjacent subsections being connected to one another at an inflection point of the function.

9. The method according to claim 1, which further comprises:
    detecting a further measured value at a further measuring time, with the further measured value also being indicative for the potential hazard within the monitoring range;
    establishing a further waiting time by way of the function; and
    determining a further triggering time based on the further measuring time and the further waiting time thus established.

10. The method according to claim 9, wherein the further measured value differs from the measured value by at least one predetermined value.

11. The method according to claim 10, which comprises:
    continuing to take into consideration the triggering time, in addition to the further triggering time, if the further measured value is greater than the measured value; and
    discarding to triggering time if the further measured value is less than the measured value.

12. The method according to claim 1, wherein the measured value is a value indicative of a concentration of a gas.

13. An alarm device for issuing an alarm, the alarm device comprising:
    a detection device configured for detecting a measured value is indicative for a hazard potential within a monitoring range; and
    an evaluation device coupled to said detection device and configured to execute the method according to claim 1.

14. A program element of a non-transitory computer readable medium for specifying a triggering point for issuance of an alarm by an alarm device which, when it is executed by an evaluation unit, is enabled to carry out the method according to claim 1.

15. A method for determining a triggering time for issuing an alarm of an alarm device, the method which comprises:
    detecting a measured value at a measuring time, the measured value being indicative of a hazard potential within a monitoring range;
    establishing a waiting time by way of a function, the function:
        specifying an assigned waiting time in each case for a plurality of different measured values, the waiting time reducing as the measured value rises and increasing as the measured value falls, for a slight increase in the measured value, the corresponding waiting time also only changes slightly; and
        having a continuous profile, the continuous profile not exhibiting jumps or discontinuities;
    determining the triggering time based on the measuring time and the waiting time thus established;

the waiting time being the time necessary to wait after the occurrence of the measured value before an alarm may be issued; and defining the function so as not to fall below a waiting-time-independent minimum threshold for the measured value, the waiting time-independent minimum threshold value represents an absolute lower boundary for the measured value below which the alarm may not be issued.

\* \* \* \* \*